United States Patent
Brough

(10) Patent No.: US 9,545,361 B1
(45) Date of Patent: Jan. 17, 2017

(54) MULTIPLE SPEED PROCESS FOR PRESERVING HEAT SENSITIVE PORTIONS OF A THERMOKINETICALLY MELT BLENDED BATCH

(75) Inventor: Chris Brough, Austin, TX (US)

(73) Assignee: DISPERSOL TECHNOLOGIES, LLC, Georgetown, TX (US)

(*) Notice: Subject to any disclaimer, the term of this patent is extended or adjusted under 35 U.S.C. 154(b) by 0 days.

(21) Appl. No.: 13/190,176

(22) Filed: Jul. 25, 2011

(51) Int. Cl.
*A61J 3/02* (2006.01)

(52) U.S. Cl.
CPC ........................................ *A61J 3/02* (2013.01)

(58) Field of Classification Search
CPC ........................................................ A61J 3/02
USPC .................................................. 366/206, 601
See application file for complete search history.

(56) References Cited

U.S. PATENT DOCUMENTS

| | | | |
|---|---|---|---|
| 3,638,917 A * | 2/1972 | Osten ............................ | 366/149 |
| 4,152,076 A * | 5/1979 | Driskill .......................... | 366/79 |
| 4,534,657 A * | 8/1985 | Clement ........................ | 366/265 |
| 4,628,073 A * | 12/1986 | Fisher ............................ | 525/70 |
| 4,764,412 A | 8/1988 | Burns et al. | |
| 4,789,597 A | 12/1988 | Gupta et al. | |
| 5,895,790 A | 4/1999 | Good | |
| 6,214,331 B1 * | 4/2001 | Vanderhoff et al. ....... | 424/78.17 |
| 6,544,503 B1 * | 4/2003 | Vanderhoff et al. ....... | 424/78.17 |
| 6,709,146 B1 * | 3/2004 | Little et al. .................. | 366/76.3 |
| 8,319,916 B2 * | 11/2012 | Matsumoto et al. ........ | 349/106 |
| 2004/0120215 A1 * | 6/2004 | Huang et al. ................ | 366/203 |
| 2005/0258288 A1 * | 11/2005 | Dalziel et al. ............... | 241/172 |
| 2006/0068011 A1 * | 3/2006 | Ebube ........................... | 424/472 |
| 2008/0219088 A1 * | 9/2008 | Wood et al. ................. | 366/170.1 |
| 2009/0053315 A1 * | 2/2009 | Brough et al. ............... | 424/489 |
| 2009/0311295 A1 * | 12/2009 | Mathiowitz et al. ........ | 424/401 |

* cited by examiner

Primary Examiner — David Sorkin
Assistant Examiner — Abbas Rashid

(57) ABSTRACT

The present disclosure is directed to compositions and methods for making a pharmaceutical composition by thermokinetic compounding, wherein the compositions include one or more thermolabile components, for example one or more active pharmaceutical ingredients (API) with one or more pharmaceutically acceptable excipients. The methods comprise thermokinetic processing of the thermolabile components into a composite by blending certain thermolabile components in a thermokinetic mixer using multiple speeds during a single, rotationally continuous operation. The composite can be further processed into pharmaceutical compositions by conventional methods known in the art, such as hot melt extrusion, melt granulation, compression molding, tablet compression, capsule filling, film-coating, or injection molding.

11 Claims, 8 Drawing Sheets

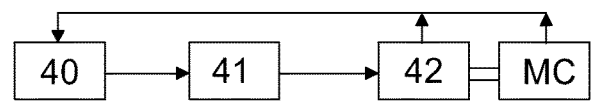
FIG. 7
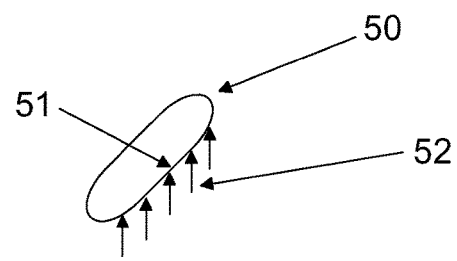
FIG. 8
PRIOR ART
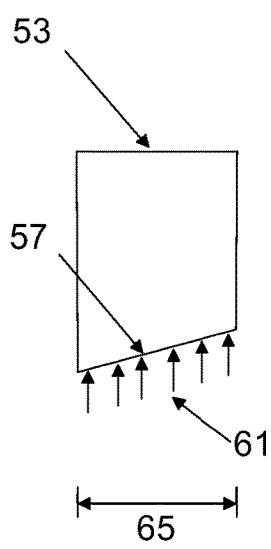 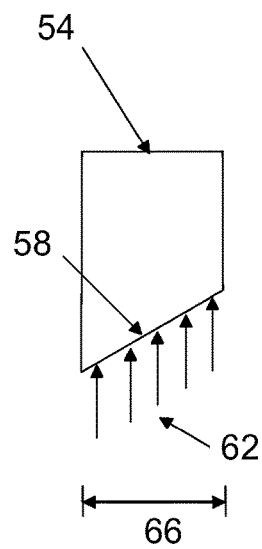 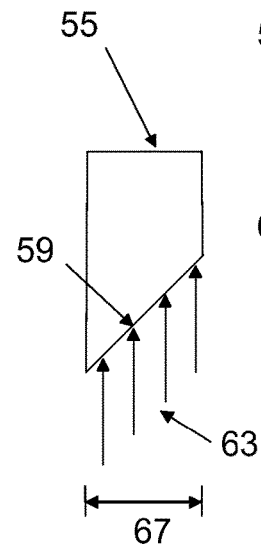 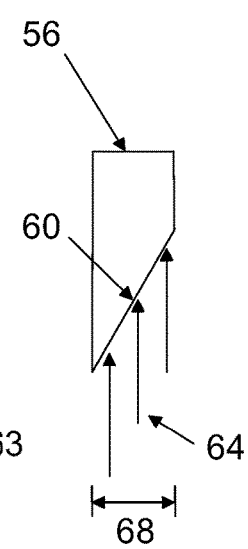
FIG. 9　　FIG. 10　　FIG. 11　　FIG. 12

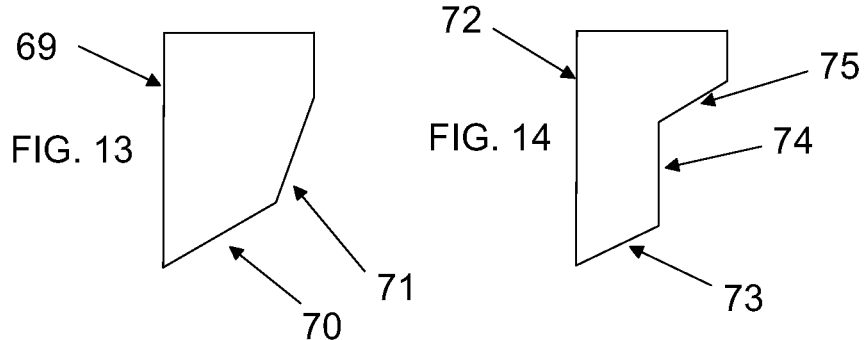
FIG. 13
FIG. 14
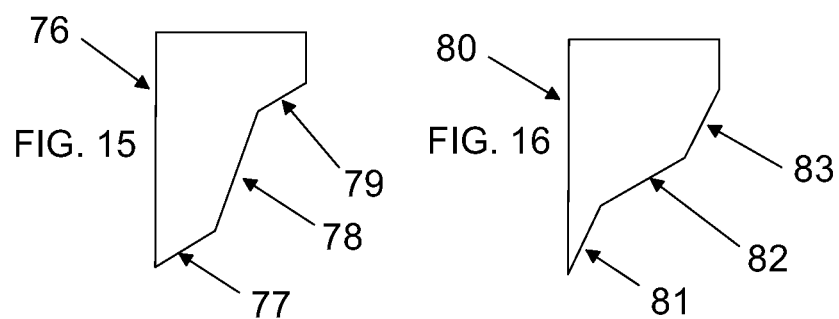
FIG. 15
FIG. 16
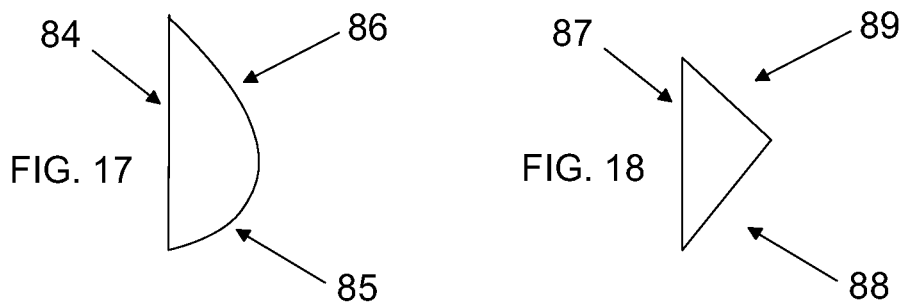
FIG. 17
FIG. 18

MULTIPLE SPEED PROCESS FOR PRESERVING HEAT SENSITIVE PORTIONS OF A THERMOKINETICALLY MELT BLENDED BATCH

RELATED APPLICATIONS

This application is related to U.S. Provisional Application Ser. No. 60/957,044, filed on Aug. 21, 2007, U.S. Provisional Application No. 61/050,922, filed on May 6, 2008, application Ser. No. 12/196,154, filed on Aug. 21, 2008, and International Patent Application PCT/US2008/073913, entitled "Thermo-Kinetic Mixing for Pharmaceutical Applications," filed on Aug. 21, 2008, the entire contents of each of which are incorporated herein by reference.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present disclosure relates in general to the field of pharmaceutical manufacturing, and more particularly, to thermokinetic mixing of active pharmaceutical ingredients (APIs) to produce novel dosage forms.

2. Description of Related Art

Current high-throughput molecular screening methods used by the pharmaceutical industry have resulted in a vast increase in the proportion of newly discovered molecular entities which are poorly water-soluble. The therapeutic potential of many of these molecules is often not fully realized either because the molecule is abandoned during development due to poor pharmacokinetic profiles, or because of suboptimal product performance. Also, in recent years the pharmaceutical industry has begun to rely more heavily on formulational methods for improving drug solubility owing to practical limitations of salt formation and chemical modifications of neutral or weakly acidic/basic drugs. Consequently, advanced formulation technologies aimed at the enhancement of the dissolution properties of poorly water-soluble drugs are becoming increasingly more important to modern drug delivery.

U.S. Pat. No. 4,789,597, issued to Gupta, is directed to the incorporation of chemically reactive agents on resin particles. Briefly, chemically reactive agents are locked to particles of suitable synthetic resins without wholly fluxing the resins. A high quality intermediate product is obtained having no premature reaction taking place, suitable for further techniques. The process includes the steps of intensively mixing and thermokinetically heating a batch of finely divided resin particles, with a chemically reactive agent, in an enclosed mixing chamber with a plurality of blades attached to arms rotating about a central axis within the chamber, and having a blade tip speed of at least about 18 meters per second, mixing the batch until the chemically reactive agent is locked to the resin particles, ensuring that temperature of the batch stays well below decomposition temperature of the reactive agent and below fluxing temperature of the resin particles, discharging the batch from the mixing chamber and cooling the discharged batch to avoid agglomeration of the resin particles.

U.S. Pat. No. 5,895,790, issued to Good, is directed to thermosetting a wide range of polymer blends. Briefly, a wide range of polymer blends and waste thermoset material can be recovered. One method of thermosetting a wide range polymer blends forms a homogenous and adaptable material. This material has a melt index of zero and a relatively predictable density. Very high levels of fibrous non-polymers may be added to the first material.

U.S. Pat. No. 6,709,146, issued to Little, is directed to a thermokinetic mixer and method of using the mixer. Briefly, a thermokinetic mixer has a mixing chamber with shaft projections removable at least in part and replaceable without cutting the projections from the shaft. In one embodiment, only a tip portion of such projections are removable and replaceable without such cutting. In another embodiment, shaft projections into the mixing chamber include a tooth having a substantially reticulated face forming a deflecting surface such that substantially all mixing chamber particles encountering the tooth strike are deflected at an incident substantially lateral angle from the deflecting surface.

U.S. Pat. No. 4,764,412, issued to Burns, discloses the use of a high speed mixer with a heated jacket about its vertical mixing chamber to first mix a set of components at 1700 rpm. The high speed mixer is stopped and after additional components are added, the rotational speed of the mixer is increased to 3400 rpm. Operation of the high speed mixer at a rotation speed of 3400 rpm generates heat which is advantageous in further processing of the mixture.

U.S. patent application Ser. No. 12/196,154, filed by the same inventor as this application and additional co-inventors, is directed to the application of thermokinetic compounding in the field of pharmaceutical manufacturing. Thermokinetic compounding is a method of thermokinetic mixing until melt blended. A pharmaceutical composition or composite made by thermokinetic compounding may be further processed according to methods well known to those of skill in the field, including but not limited to hot melt extrusion, melt granulation, compression molding, tablet compression, capsule filling, film-coating, or injection molding into a final product. One embodiment is directed to a method of making a pharmaceutical composition that includes one or more active pharmaceutical ingredients with one or more pharmaceutically acceptable excipients by the thermokinetic compounding process. Another embodiment is directed to the composite comprising one or more APIs with one or more pharmaceutically acceptable excipients made by thermokinetic compounding is the final product.

Although the application of thermokinetic compounding in the field of pharmaceutical manufacturing offers significant advantages over other methodologies known in the pharmaceutical arts, it is possible that issues can arise in continuously melt blending certain heat sensitive or thermolabile components with certain non-thermolabile components using a thermokinetic mixer. Blending such a combination of components often requires using an elevated shaft speed or a reduced shaft speed for an extended processing time sufficient to impart complete amorphosity on the fully processed batch. In certain cases, this results in an exceedance of a limit temperature or heat input for an unacceptable duration. The batch thus experiences unacceptable degradation of the thermolabile components, as the substantial amount of heat absorbed by the entire batch results in thermal degradation of thermolabile components instead of increasing overall batch temperature. Substantially complete amorphosity is a measure well-known in the art of pharmaceutical preparation and processing; bioavailability may be significantly impaired in compositions lacking substantially complete amorphosity.

BRIEF SUMMARY OF THE INVENTION

The present disclosure unexpectedly solves the issues associated with blending certain heat sensitive or thermolabile components in a thermokinetic mixer by using multiple speeds during a single, rotationally continuous operation on a batch containing thermolabile components. Identified herein is a novel thermokinetic mixer and mixing process that can blend heat sensitive or thermolabile components while minimizing any substantial thermal degradation. In particular, the disclosure is useful in processing mixtures that include thermolabile components whose exposure to a melt temperature or a cumulative heat input over a defined time period results in substantial degradation. The resulting pharmaceutical compositions have increased bioavailability and stability. In addition, the methods disclosed herein are easily scalable to commercial production of pharmaceutical compositions.

One embodiment of the present disclosure is a method for continuous blending and melting of an autoheated mixture in the mixing chamber of a high speed mixer, where a first speed is changed mid-processing to a second speed upon achieving a first desired process parameter. In another embodiment, the second speed may be maintained until a final process parameter is achieved, whereupon shaft rotation is stopped and a melt blended batch is withdrawn or ejected from the mixing chamber for further processing. In another embodiment, one or more intermediate speed changes may be made to the shaft rotational speed between the second speed and stopping the shaft rotation. Process parameters which determine shaft speed changes are predetermined and may be sensed and displayed, calculated, inferred, or otherwise established with reasonable certainty so that the speed change(s) are made during a single, rotationally continuous processing of a batch in a mixing chamber of the high speed mixer. Another embodiment is the use of variations in the shape, width and angle of the facial portions of the shaft extensions or projections that intrude into the main processing volume to control translation of rotational shaft energy delivered to the extensions or projections into heating energy within particles impacting the portions of the extensions or projections.

The present inventor investigated the melt blending of various mixtures including thermolabile components in a thermokinetic mixing chamber. The present inventor unexpectedly found that using multiple speeds during a single, rotationally continuous operation on certain batches containing thermolabile components solved the problem of exceeding a limit temperature or excessive heat input for the batch. The present inventor also surprisingly found that varying the shape, width and angle away from a shaft axis plane of a shaft extension or projection provided a method of controlling the shear delivered to a particle, which in turn provided control over shaft energy translated into heat energy available for softening or melting a polymer part of a particle in a thermokinetic mixing chamber.

An embodiment of the present disclosure is a method of blending a composition of two or more ingredients, wherein the ingredients comprise one or more heat sensitive or thermolabile components, wherein the resulting composition is amorphous, homogenous, heterogenous, or heterogeneously homogenous, the method comprising mixing the ingredients in a thermokinetic mixing chamber, wherein a thermokinetic mixer shaft is operated at a first speed until achieving a predetermined parameter, at which time the shaft speed is adjusted to a second speed for a second time period, wherein the mixing process is substantially uninterrupted between the first and second time periods. In another embodiment of the present disclosure, the thermokinetic mixer shaft is operated at one or more speeds until achieving a predetermined parameter, at which time the shaft speed is adjusted to a different speed for a different time period, wherein the mixing process is substantially uninterrupted between the two or more time periods. An example of such an embodiment is a method of blending a composition of two or more ingredients, wherein a thermokinetic mixer shaft is operated at a first speed until achieving a predetermined parameter, at which time the shaft speed is adjusted to a second speed for a second time period, wherein the mixing process is substantially uninterrupted between the first and second time periods, and wherein at the end of the second time period a rotational speed of the shaft is changed from the second speed to a third speed for a third time period upon achieving a predetermined parameter. In one embodiment, the mixing process is substantially uninterrupted between the second and third time periods.

In certain embodiments, the heat sensitive or thermolabile components may comprise one or more active pharmaceutical ingredients, one or more pharmaceutically acceptable excipients, or one or more pharmaceutically acceptable heat sensitive polymers. In other embodiments, the heat sensitive or thermolabile components may comprise one or more active pharmaceutical ingredients and one or more pharmaceutically acceptable excipients or heat sensitive polymers. In other embodiments, the active pharmaceutical ingredients and one or more pharmaceutically acceptable excipients are added in a ratio of from about 1:2 to 1:9, respectively. In still other embodiments, the active pharmaceutical ingredients and one or more pharmaceutically acceptable heat sensitive polymers are added in a ratio of from about 1:2 to 1:9, respectively. In certain embodiments, the second time period may be at least about five percent, 10 percent, 15 percent, 20 percent, 25 percent or more of the first time period. In other embodiments, the speed during the second time period is increased by about 100 revolutions per minute ("RPM"), 200 RPM, 300 RPM, 400 RPM, 500 RPM, 600 RPM, 700 RPM, 800 RPM, 900 RPM, 1000 RPM, 1100 RPM, 1200 RPM, 1300 RPM, 1400 RPM, 1500 RPM, 1600 RPM, 1700 RPM, 1800 RPM, 1900 RPM, 2000 RPM, 2100 RPM, 2200 RPM, 2300 RPM, 2400 RPM, 2500 RPM, or more as compared to the speed during the first time period. For example, in one embodiment the first speed is greater than 1000 RPM and the second speed is 200 to 400 RPM greater than the first speed. In another embodiment, the first speed is greater than 1000 RPM and the second speed is 200 to 1000 RPM greater than the first speed. In still another embodiment, the first speed is greater than 1000 RPM and the second speed is 200 to 2500 RPM greater than the first speed.

In one embodiment, the end of the first time period is substantially before the mixing chamber temperature reaches the shear transition temperature or melting point of any substantial component of the ingredients. In another embodiment, the end of the first time period is a predetermined time period and a change to the second speed is made automatically by the thermokinetic mixer at the end of the first time period. In yet another embodiment, the end of the first time period is substantially before the mixing chamber temperature reaches the shear transition temperature of an active pharmaceutical ingredient in the ingredients. In still another embodiment, the end of the first time period is substantially before mixing chamber temperature reaches the shear transition temperature of an excipient in the ingredients. In another embodiment, the end of the first time period is substantially before mixing chamber temperature reaches the shear transition temperature of a heat sensitive polymer in the ingredients.

In one embodiment, the end of the second or any subsequent time period is substantially before an active pharmaceutical ingredient experiences substantial thermal degradation. In another embodiment, the end of the second or any subsequent time period is substantially before an excipient ingredient experiences substantial thermal degradation. In yet another embodiment, the end of the second or any subsequent time period is substantially before a heat sensitive polymer ingredient experiences substantial thermal degradation. In one embodiment, at the end of the second or any subsequent time period the active pharmaceutical ingredient and an excipient of the ingredients are substantially amorphous. In another embodiment, at the end of the second or any subsequent time period the active pharmaceutical ingredient and a heat sensitive polymer of the ingredients are substantially amorphous. In other embodiments, upon achieving a final process parameter, the shaft rotation is stopped and a batch or composite is withdrawn or ejected from the mixing chamber for further processing. In certain embodiments, the batch or composite is withdrawn or ejected at or below the glass transition temperature of at least one of the components of the batch or composite. In other embodiments, the batch or composite is further processed by hot melt extrusion, melt granulation, compression molding, tablet compression, capsule filling, film-coating, or injection molding. In other embodiments, the batch or composite is withdrawn or ejected at the beginning of a RPM plateau, for example before degradation occurs in the batch or composite. In other embodiments, the RPM deceleration prior to withdrawal or ejection of the batch or composite is modulated to produce a more uniform batch or composite.

Another embodiment of the present disclosure is directed to a method of compounding one or more active pharmaceutical ingredients and at least one polymeric pharmaceutically acceptable excipient to produce an amorphous, homogenous, heterogenous, or heterogeneously homogenous composition, the method comprising thermokinetic mixing of the active pharmaceutical ingredient(s) and at least one polymeric pharmaceutically acceptable excipient in a chamber at a first speed effective to increase the temperature of the mixture, and at a time point at which the temperature is below the shear transition temperature of any active pharmaceutical ingredient or polymeric pharmaceutically acceptable excipient in the mixture, increasing the mixer rotation to a second speed to produce an amorphous, homogenous, heterogenous, or heterogeneously homogenous composition, wherein the increase is accomplished without stopping the mixing or opening the chamber. In another embodiment of the present disclosure, the method comprises thermokinetic mixing in a chamber at one or more speeds effective to increase the temperature of the mixture, at which time the shaft speed is adjusted to a different speed for a different time period, and at a time point at which the temperature is below the shear transition temperature of any active pharmaceutical ingredient or polymeric pharmaceutically acceptable excipient in the mixture, and increasing the mixer rotation to one or more different speeds, wherein the increase is accomplished without stopping the mixing or opening the chamber.

Certain embodiments of the present disclosure are directed to thermokinetic mixers used to produce a pharmaceutical composition comprising one or more heat sensitive or thermolabile components. Various embodiments of the mixer may comprise one or more and any combination of the following: (1) a mixing chamber, for example a substantially cylindrical mixing chamber; (2) a shaft disposed through the center axis of the mixing chamber; (3) an electric motor connected to the shaft, for example which is effective to impart rotational motion to the shaft; (4) one or more projections or extensions from the shaft and perpendicular to the long axis of the shaft; (5) one more heat sensors, for example attached to a wall of the mixing chamber and operative to detect heat or temperature of at least a portion of the interior of the mixing chamber; (6) a variable frequency device, for example connected to the motor; (7) a door disposed in a wall of the mixing chamber, for example which is effective when opened during a process run to allow the contents of the mixing chamber to pass out of the mixing chamber; and (8) an electronic controller. In certain embodiments, a hygroscopic condition is maintained within the thermokinetic mixer. In other embodiments, the thermokinetic mixers are designed to maximize shear during batch processing.

In certain embodiments, the electronic controller is in communication with the temperature sensors, the door and the variable frequency device. In some embodiments, the electronic controller comprises a user input device, a timer, an electronic memory device configured to accept user input of process parameters or predetermined parameters for two or more stages of a thermokinetic mixing processing, and a display. In an embodiment, the process parameters or predetermined parameters are saved in the memory device and displayed on the monitor for one or more stages of a process run. In certain embodiments, when one of the predetermined parameters is met during a stage of a processing run, the electronic controller automatically moves the process run to the subsequent stage. In other embodiments, the mixing chamber is interiorly lined by interior liner pieces. The liner pieces may be made of material that minimizes any stickiness of the batch during processing, for example stainless steel and other such steel alloys, titanium alloys (such as nitrided or nitride-containing titanium), and wear and heat resistant polymers (such as Teflon®).

In one embodiment of the present disclosure, at least one of the temperature sensors detects infrared radiation, for example wherein the radiation level is output as temperature on the display. In other embodiments, the predetermined parameters may be any one or a combination of the following: temperature, rate of temperature change, shaft rotational speed (e.g., rate of acceleration and deceleration), amperage draw of the electric motor, time of stage, or rate of withdrawal or exit of the batch or composite. One of skill in the art will be able to change each of the following parameters to obtain a batch or composite with the desired characteristics through routine experimentation. In another embodiment, the output display may be any one or a combination of the following: chamber temperature, motor revolutions per minute, amperage draw of the motor, or cycle elapsed time.

In certain embodiments of the present disclosure, the one or more projections or extensions from the shaft comprise a base and an end portion, and, for example, the end portion may be removable from the base portion and the base portion may be removable from the shaft. In other embodiments, the projections or extensions are replaceable in the thermokinetic mixer, for example based on wear and tear or different batch parameters. In one embodiment, the one or more projections or extensions from the shaft comprise one or more main facial portions having a width of at least about 0.75 inches, at an angle of between 15 to 80 degrees from a shaft axis plane. In other embodiments, the one or more projections or extensions from the shaft comprise one or more main facial portions having a width of at least about 0.80 inches, 0.85 inches, 0.90 inches, 0.95 inches, 1.0 inches, 1.1 inches, 1.2 inches, 1.3 inches, 1.4 inches, 1.5 inches, 1.6 inches, 1.7 inches, 1.8 inches, 1.9 inches, 2.0 inches, 2.1 inches, 2.2 inches, 2.3 inches, 2.4 inches, 2.5 inches, 2.6 inches, 2.7 inches, 2.8 inches, 2.9 inches, 3.0 inches, 3.1 inches, 3.2 inches, 3.3 inches, 3.4 inches, 3.5 inches, 3.6 inches, 3.7 inches, 3.8 inches, 3.9 inches, 4.0 inches, 4.1 inches, 4.2 inches, 4.3 inches, 4.4 inches, 4.5 inches, 4.6 inches, 4.7 inches, 4.8 inches, 4.9 inches, 5.0 inches, or greater, at an angle of about 15, 20, 25, 30, 35, 40, 45, 50, 55, 60, 65, 70, 75, or 80 degrees from a shaft axis plane. In certain embodiment, the one or more projections or extensions from the shaft control translation of rotational shaft energy delivered to the projections or extensions into heating energy within particles impacting the projections.

In other embodiments, these dimensions of the one or more projections or extensions from the shaft are designed to increase the shear profile of the population of shear-resistant particles in the batch, for example to produce substantially amorphous composites. In certain embodiments, the dimensions of the one or more projections or extensions from the shaft are designed to produce composites that are at least about 60, 65, 70, 75, 80, 85, 90, 95, or 99 percent amorphous.

BRIEF DESCRIPTION OF THE SEVERAL VIEWS OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 7. A graph block diagram of a thermokinetic mixer process at two or more rotational shaft speeds.

FIG. 8. A cross section of a main facial portion of a prior art shaft extension.

FIG. 9. A cross section of a main facial portion of a shaft extension with a shaft axial plane at an angle of about 15 degrees.

FIG. 10. A cross section of a main facial portion of a shaft extension with a shaft axial plane at an angle of about 30 degrees.

FIG. 11. A cross section of a main facial portion of a shaft extension with a shaft axial plane at an angle of about 45 degrees.

FIG. 12. A cross section of a main facial portion of a shaft extension with a shaft axial plane at an angle of about 60 degrees.

FIG. 13. An alternative design of a cross section of a main facial portion of a shaft extension.

FIG. 14. An alternative design of a cross section of a main facial portion of a shaft extension.

FIG. 15. An alternative design of a cross section of a main facial portion of a shaft extension.

FIG. 16. An alternative design of a cross section of a main facial portion of a shaft extension.

FIG. 17. An alternative design of a cross section of a main facial portion of a shaft extension.

FIG. 18. An alternative design of a cross section of a main facial portion of a shaft extension.

DETAILED DESCRIPTION OF THE INVENTION

Figure 1:
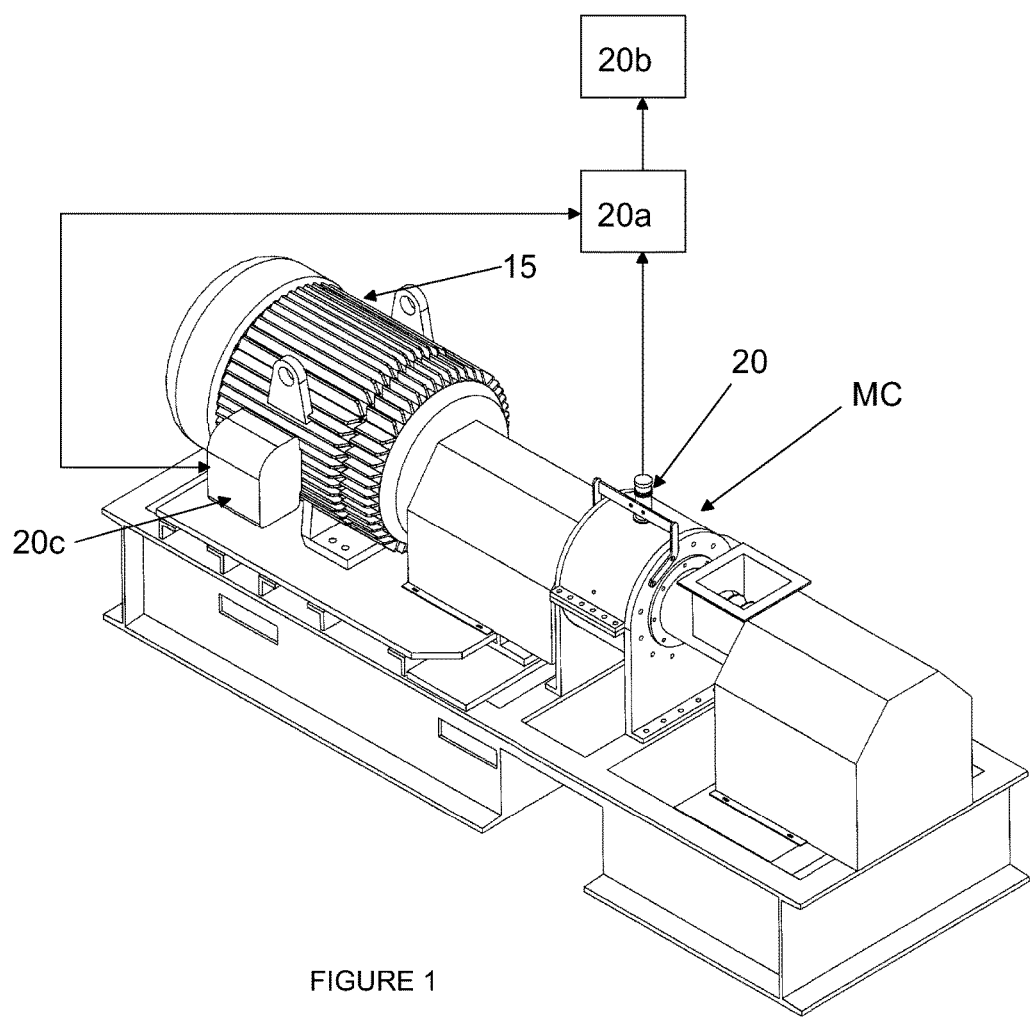
FIG. 1. A view of the thermokinetic mixer assembly.

Although making and using various embodiments of the present disclosure are discussed in detail below, it should be appreciated that the present disclosure provides many inventive concepts that may be embodied in a wide variety of contexts. The specific aspects and embodiments discussed herein are merely illustrative of ways to make and use the disclosure, and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. With regard to the values or ranges recited herein, the term "about" is intended to capture variations above and below the stated number that may achieve substantially the same results as the stated number. In the present disclosure, each of the variously stated ranges is intended to be continuous so as to include each numerical parameter between the stated minimum and maximum value of each range. For Example, a range of about 1 to about 4 includes about 1, 1, about 2, 2, about 3, 3, about 4, and 4. The terminology herein is used to describe specific embodiments of the disclosure, but their usage does not delimit the disclosure, except as outlined in the claims.

As used herein, the term "thermokinetic compounding" or "TKC" refers to a method of thermokinetic mixing until melt blended. TKC may also be described as a thermokinetic mixing process in which processing ends at a point sometime prior to agglomeration.

As used herein, the term "main facial portion" refers to the "top face" of a shaft extension. The top face of a shaft extension is the face facing the inside wall of the mixing chamber of a thermokinetic mixer.

As used herein, the term "shear transition temperature" refers to the point at which further energy input does not result in an immediate rise in temperature.

As used herein, the phrase "a homogenous, heterogenous, or heterogeneously homogenous composite or an amorphous composite" refers to the various compositions that can be made using the TKC method.

As used herein, the term "heterogeneously homogeneous composition" refers to a material composition having at least two different materials that are evenly and uniformly distributed throughout the volume.

As used herein, "bioavailability" is a term meaning the degree to which a drug becomes available to the target tissue after being administered to the body. Poor bioavailability is a significant problem encountered in the development of pharmaceutical compositions, particularly those containing an active ingredient that is not highly soluble. In certain embodiments such as formulations of proteins, the proteins may be water soluble, poorly soluble, not highly soluble, or not soluble. The skilled artisan will recognize that various methodologies may be used to increase the solubility of proteins, e.g., use of different solvents, excipients, carriers, formation of fusion proteins, targeted manipulation of the amino acid sequence, glycosylation, lipidation, degradation, combination with one or more salts and the addition of various salts.

As used herein, the phrase "pharmaceutically acceptable" refers to molecular entities, compositions, materials, excipients, carriers, and the like that do not produce an allergic or similar untoward reaction when administered to humans in general.

As used herein, the term "active pharmaceutical ingredient" or "API" is interchangeable with the terms "drug," "drug product," "medication," "liquid," "biologic," or "active ingredient." As used herein, an "API" is any component intended to furnish pharmacological activity or other direct effect in the diagnosis, cure, mitigation, treatment, or prevention of disease, or to affect the structure or any function of the body of humans or other animals. In certain embodiments, the aqueous solubility of the API may be poorly soluble.

Examples of APIs that may be utilized in the present disclosure include, but are not limited to, antibiotics, analgesics, vaccines, anticonvulsants, anti-diabetic agents, anti-fungal agents, anti-neoplastic agents, anti-parkinsonian agents, anti-rheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, anti-hypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. In certain embodiments, the API is a poorly water-soluble drug or a drug with a high melting point.

The API may be found in the form of one or more pharmaceutically acceptable salts, esters, derivatives, analogs, prodrugs, and solvates thereof. As used herein, a "pharmaceutically acceptable salt" is understood to mean a compound formed by the interaction of an acid and a base, the hydrogen atoms of the acid being replaced by the positive ion of the base. Non-limiting examples of pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate. Another method for defining the ionic salts may be as an acidic functional group, such as a carboxylic acid functional group, and a pharmaceutically acceptable inorganic or organic base. Non-limiting examples of bases include, but are not limited to, hydroxides of alkali metals such as sodium, potassium and lithium; hydroxides of calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

A variety of administration routes are available for delivering the APIs to a patient in need. The particular route selected will depend upon the particular drug selected, the weight and age of the patient, and the dosage required for therapeutic effect. The pharmaceutical compositions may conveniently be presented in unit dosage form. The APIs suitable for use in accordance with the present disclosure, and their pharmaceutically acceptable salts, derivatives, analogs, prodrugs, and solvates thereof, can be administered alone, but will generally be administered in admixture with a suitable pharmaceutical excipient, diluent, or carrier selected with regard to the intended route of administration and standard pharmaceutical practice.

The APIs may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

The excipients and adjuvants that may be used in the presently disclosed compositions and composites, while potentially having some activity in their own right, for example, antioxidants, are generally defined for this application as compounds that enhance the efficiency and/or efficacy of the active ingredients. It is also possible to have more than one active ingredient in a given solution, so that the particles formed contain more than one active ingredient.

As stated, excipients and adjuvants may be used to enhance the efficacy and efficiency of the APIs. Non-limiting examples of compounds that can be included are binders, cryoprotectants, lyoprotectants, surfactants, fillers, stabilizers, polymers, protease inhibitors, antioxidants and absorption enhancers. The excipients may be chosen to modify the intended function of the active ingredient by improving flow, or bio-availability, or to control or delay the release of the API. Specific nonlimiting examples include: sucrose, trehaolose, Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphaditylcholine, glycolic acid and salts, deoxycholic acid and salts, sodium fusidate, cyclodextrins, polyethylene glycols, labrasol, polyvinyl alcohols, polyvinyl pyrrolidones and tyloxapol. Using the process of the present disclosure, the morphology of the active ingredients can be modified, resulting in highly porous microparticles and nanoparticles.

Exemplary thermal binders that may be used in the presently disclosed compositions and composites include but are not limited to polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, and xanthan gum. One embodiment of the binder is poly(ethylene oxide) (PEO), which can be purchased commercially from companies such as the Dow Chemical Company, which markets PEO under the POLY OX™ trademark exemplary grades of which can include WSR N80 having an average molecular weight of about 200,000; 1,000,000; and 2,000,000.

Suitable grades of PEO can also be characterized by viscosity of solutions containing fixed concentrations of PEO, such as for example:

| POLYOX Water-Soluble Resin NF | Viscosity Range Aqueous Solution at 25° C., mPa · s |
| --- | --- |
| POLYOX Water-Soluble Resin NF WSR N-10 | 30-50 (5% solution) |
| POLYOX Water-Soluble Resin NF WSR N-80 | 55-90 (5% solution) |
| POLYOX Water-Soluble Resin NF WSR N-750 | 600-1,200 (5% solution) |
| POLYOX Water-Soluble Resin NF WSR-205 | 4,500-8,800 (5% solution) |
| POLYOX Water-Soluble Resin NF WSR-1105 | 8,800-17,600 (5% solution) |
| POLYOX Water-Soluble Resin NF WSR N-12K | 400-800 (2% solution) |
| POLYOX Water-Soluble Resin NF WSR N-60K | 2,000-4,000 (2% solution) |
| POLYOX Water-Soluble Resin NF WSR-301 | 1,650-5,500 (1% solution) |
| POLYOX Water-Soluble Resin NF WSR Coagulant | 5,500-7,500 (1% solution) |
| POLYOX Water-Soluble Resin NF WSR-303 | 7,500-10,000 (1% solution) |

Suitable thermal binders that may or may not require a plasticizer include, for example, Eudragit™ RS PO, Eudragit™ S100, Kollidon SR (poly(vinyl acetate)-co-poly(vinylpyrrolidone) copolymer), Ethocel™ (ethylcellulose), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methyl-methacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit L-100-55™ (MA-EA, 1:1), hydroxypropylmethylcellulose acetate succinate (HPMCAS), Coateric™ (PVAP), Aquateric™ (CAP), and AQUACOAT™ (HPMCAS), polycaprolactone, starches, pectins; polysaccharides such as tragacanth, gum arabic, guar gum, and xanthan gum.

The stabilizing and non-solubilizing carrier may also contain various functional excipients, such as: hydrophilic polymer, antioxidant, super-disintegrant, surfactant including amphiphilic molecules, wetting agent, stabilizing agent, retardant, similar functional excipient, or combination thereof, and plasticizers including citrate esters, polyethylene glycols, PG, triacetin, diethylphthalate, castor oil, and others known to those or ordinary skill in the art. Extruded material may also include an acidifying agent, adsorbent, alkalizing agent, buffering agent, colorant, flavorant, sweetening agent, diluent, opaquant, complexing agent, fragrance, preservative or a combination thereof.

Exemplary hydrophilic polymers which can be a primary or secondary polymeric carrier that can be included in the composites or composition disclosed herein include poly(vinyl alcohol) (PVA), polyethylene-polypropylene glycol (e.g. POLOXAMER™), carbomer, polycarbophil, or chitosan. Hydrophilic polymers for use with the present disclosure may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethylcellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

By "immediate release" is meant a release of an active agent to an environment over a period of seconds to no more than about 30 minutes once release has begun and release begins within no more than about 2 minutes after administration. An immediate release does not exhibit a significant delay in the release of drug.

By "rapid release" is meant a release of an active agent to an environment over a period of 1-59 minutes or 0.1 minute to three hours once release has begun and release can begin within a few minutes after administration or after expiration of a delay period (lag time) after administration.

As used herein, the term "extended release" profile assumes the definition as widely recognized in the art of pharmaceutical sciences. An extended release dosage form will release the drug (i.e., the active agent or API) at a substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms).

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered.

The term "controlled release", as regards to drug release, includes the terms "extended release", "prolonged release", "sustained release", or "slow release", as these terms are used in the pharmaceutical sciences. A controlled release can begin within a few minutes after administration or after expiration of a delay period (lag time) after administration.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

The term "mixed release" as used herein refers to a pharmaceutical agent that includes two or more release profiles for one or more active pharmaceutical ingredients. For example, the mixed release may include an immediate release and an extended release portion, each of which may be the same API or each may be a different API.

A timed release dosage form is one that begins to release drug after a predetermined period of time as measured from the moment of initial exposure to the environment of use.

A targeted release dosage form generally refers to an oral dosage form that is designed to deliver drug to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can deliver to other sections of the gastrointestinal tract such as the stomach, jejunum, ileum, duodenum, cecum, large intestine, small intestine, colon, or rectum.

By "delayed release" is meant that initial release of drug occurs after expiration of an approximate delay (or lag) period. For example, if release of drug from an extended release composition is delayed two hours, then release of the drug begins at about two hours after administration of the composition, or dosage form, to a subject. In general, a delayed release is opposite of an immediate release, wherein release of drug begins after no more than a few minutes after administration. Accordingly, the drug release profile from a particular composition can be a delayed-extended release or a delayed-rapid release. A "delayed-extended" release profile is one wherein extended release of drug begins after expiration of an initial delay period. A "delayed-rapid" release profile is one wherein rapid release of drug begins after expiration of an initial delay period.

A pulsatile release dosage form is one that provides pulses of high active ingredient concentration, interspersed with low concentration troughs. A pulsatile profile containing two peaks may be described as "bimodal." A pulsatile profile of more than two peaks may be described as multi-modal.

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

The resulting composites or compositions disclosed herein may also be formulated to exhibit enhanced dissolution rate of a formulated poorly water soluble drug.

An example of a composition or formulation having a stable release profile follows. Two tablets having the same formulation are made. The first tablet is stored for one day under a first set of conditions, and the second tablet is stored for four months under the same first set of conditions. The release profile of the first tablet is determined after the single day of storage and the release profile of the second tablet is determined after the four months of storage. If the release profile of the first tablet is approximately the same as the release profile of the second tablet, then the tablet/film formulation is considered to have a stable release profile.

Another example of a composition or formulation having a stable release profile follows. Tablets A and B, each comprising a composition according to the present disclosure, are made, and Tablets C and D, each comprising a composition not according to the present disclosure, are made. Tablets A and C are each stored for one day under a first set of conditions, and tablets B and D are each stored for three months under the same first set of conditions. The release profile for each of tablets A and C is determined after the single day of storage and designated release profiles A and C, respectively. The release profile for each of tablet B and D is determined after the three months of storage and designated release profiles B and D, respectively. The differences between release profiles A and B are quantified as are the differences between release profiles C and D. If the difference between the release profiles A and B is less than the difference between release profiles C and D, tablets A and B are understood to provide a stable or more stable release profile.

Specifically, the TKC process can be used for one or more of the following pharmaceutical applications.

Dispersion of one or more APIs, wherein the API is a small organic molecule, protein, peptide, or polynucleic acid; in polymeric and/or non-polymeric pharmaceutically acceptable materials for the purpose of delivering the API to a patient via oral, pulmonary, parenteral, vaginal, rectal, urethral, transdermal, or topical routes of delivery.

Dispersion of one or more APIs, wherein the API is a small organic molecule, protein, peptide, or polynucleic acid; in polymeric and/or non-polymeric pharmaceutically acceptable materials for the purpose of improving the oral delivery of the API by improving the bioavailability of the API, extending the release of the API, targeting the release of the API to specific sites of the gastrointestinal tract, delaying the release of the API, or producing pulsatile release systems for the API.

Dispersion of one or more APIs, wherein the API is a small organic molecule, protein, peptide, or polynucleic acid; in polymeric and/or non-polymeric pharmaceutically acceptable materials for the purpose of creating bioerodable, biodegradable, or controlled release implant delivery devices.

Producing solid dispersions of thermolabile APIs by processing at low temperatures for very brief durations.

Producing solid dispersions of APIs in thermolabile polymers and excipients by processing at low temperatures for very brief durations.

Rendering a small organic API amorphous while dispersing in a polymeric, non-polymeric, or combination excipient carrier system.

Dry milling of crystalline API to reduce the particle size of the bulk material.

Wet milling of crystalline API with a pharmaceutically acceptable solvent to reduce the particle size of the bulk material.

Melt milling of a crystalline API with one or more molten pharmaceutical excipients having limited miscibility with the crystalline API to reduce the particle size of the bulk material.

Milling crystalline API in the presence of polymeric or non-polymeric excipient to create ordered mixtures where fine drug particles adhere to the surface of excipient particles and/or excipient particles adhere to the surface of fine drug particles.

Producing heterogeneously homogenous composites or amorphous composites of two or more pharmaceutical excipients for post-processing, e.g., milling and sieving, which are subsequently utilized in secondary pharmaceutical operations well known to those of skill in the art, e.g., film coating, tableting, wet granulation and dry granulation, roller compaction, hot melt extrusion, melt granulation, compression molding, capsule filling, and injection molding.

Producing single phase, miscible composites of two or more pharmaceutical materials previously considered to be immiscible for utilization in a secondary processing step, e.g. melt extrusion, film coating, tableting and granulation.

Pre-plasticizing polymeric materials for subsequent use in film coating or melt extrusion operations.

Rendering a crystalline or semi-crystalline pharmaceutical polymer amorphous, which can be used as a carrier for an API in which the amorphous character improves the dissolution rate of the API-polymer composite, the stability of the API-polymer composite, and/or the miscibility of the API and the polymer.

Deaggregate and disperse engineered particles in a polymeric carrier without altering the properties of the engineered particles.

Simple blending of an API in powder form with one or more pharmaceutical excipients.

Producing composites comprising one or more high melting point APIs and one or more thermolabile polymers without the use of processing agents.

Homogenously dispersing a coloring agent or opacifying agent within a polymer carrier or excipient blend.

In the following detailed description of preferred embodiments of the present disclosure, reference is made to the figures in the drawings, in which the same numeral refers to an identical or similar part in different figures.

The present disclosure is directed to a novel thermokinetic mixer and mixing process that can blend heat sensitive or thermolabile components without substantial thermal degradation. In particular, the disclosure is useful in processing mixtures that include thermolabile components whose exposure to a melt temperature or a cumulative heat input over a defined time period results in degradation. One embodiment of present disclosure is directed to a method for a continuous melt blend of an autoheated mixture in the mixing chamber of a high speed thermokinetic mixer, where a first speed is changed mid-process to a second speed upon achieving a first desired or predetermined process parameter. In other embodiments, the second speed is changed mid-process to a third speed upon achieving a second desired or predetermined process parameter. Additional speed changes are also within the scope of the present disclosure, as dictated by the number of desired or predetermined processing parameters needed to produce the desired composition or composite.

This process is especially applicable for producing solid dispersions of thermolabile APIs by processing at low temperatures for very brief durations at multiple speeds, producing solid dispersions of APIs in thermolabile polymers and excipients by processing at low temperatures for very brief durations at multiple speeds, producing solid dispersions of APIs in thermolabile excipients by processing at low temperatures for very brief durations at multiple speeds, and producing solid dispersions of heat sensitive polymers by processing at low temperatures for relatively brief durations at multiple speeds.

One embodiment is to use two or more different speeds during thermokinetic processing of a batch to reduce required processing time after a shear transition temperature of a portion of the batch is reached. Another embodiment is to use two or more different speeds during thermokinetic processing of a batch to reduce required processing time where the batch reaches a temperature whereafter a substantial amount of heat generated by frictional contact with shaft extensions and/or an inside surface of the mixing chamber produces thermal degradation of one or more components of the batch, and reducing the speed. Yet a further embodiment is to use two or more different speeds during thermokinetic processing of a batch to reduce required processing time where the batch reaches a temperature whereafter a substantial amount of heat generated by frictional contact with shaft extensions and/or an inside surface of the mixing chamber does not result in an overall temperature increase for the batch. Yet a further embodiment is to provide a thermokinetic processing method using two speeds to reduce thermal degradation of thermolabile or heat sensitive polymers or components of a batch processed thereby.

In one embodiment, at least a portion of a batch in the mixing chamber of the high speed mixer comprises heat sensitive or thermolabile components whose exposure to a limit temperature or limit of cumulative heat input over a defined time period must be substantially prevented or limited to obtain a melt blended batch with acceptable degradation of the heat sensitive or thermolabile components. In this embodiment, at least one of the speed changes between a start and end of the process is made so that the limit temperature or limit of heat input is not exceeded, thereby preserving the heat sensitive or thermolabile components in the composition or composite.

Thermolabile components include, but are not limited to, thermolabile APIs, excipients or polymers. Heat sensitive polymers include, but are not limited to, nylon, polytrimethylene terephthalate, polybutene-1, polybutylene terephthalate, polyethylene terephthalate, polyolefins such as polypropylene and high-density or low-density polyethylene, and mixtures or copolymers thereof, which polymers can be subject to surface and bulk polymer deficiencies as well as extrusion limitations. Other heat sensitive polymers include poly (methylmethacrylate), polyacetal, polyionomer, EVA copolymer, cellulose acetate, hard polyvinylchloride and polystyrene or copolymers thereof. A limit temperature in the disclosed process for such heat sensitive polymers may be chosen by maintaining sensed temperature of a batch within an acceptable range from the well known degradation temperature for that polymer, such as about 5, 10, 20, 25, 30, 35, 40, 45, 50, 55, 60, 65, 70, 75, 80, 85, 90, 95, or 100 degrees Celsius from a temperature at which it is known in the art that heat sensitive polymers begin to undergo degradation of a desired process parameter.

One embodiment of the present disclosure is a method for continuous blending and melting of an autoheated mixture in the mixing chamber of a high speed mixer, where a first speed is changed mid-processing to a second speed upon achieving a first desired or predetermined process parameter. In one embodiment, the second speed is maintained until a final desired or predetermined process parameter is achieved, whereupon shaft rotation is stopped and a melt blended batch is withdrawn or ejected from the mixing chamber for further processing. The shaft operates at one or more intermediate rotational speeds between changing to the second speed and stopping the shaft rotation. Process parameters which determine shaft speed changes are predetermined and may be sensed and displayed, calculated, inferred, or otherwise established with reasonable certainty so that the speed change(s) is made during a single, rotationally continuous processing of a batch in a mixing chamber of the high speed mixer. Process parameters include without limitation temperature, motor RPM, amperage draw, and time.

This disclosure is also directed to a thermokinetic mixer that can blend heat sensitive or thermolabile components without substantial thermal degradation. One embodiment of the thermokinetic mixer has a high horsepower motor driving the rotation of a horizontal shaft with teeth-like protrusions that extend outward normal to the rotational axis of the shaft. The shaft is connected to a drive motor. The portion of the shaft containing the protrusions is contained within an enclosed vessel where the compounding operation takes place, i.e., a thermokinetic mixing chamber. The high rotational velocity of the shaft coupled with the design of the shaft protrusions imparts kinetic energy onto the materials being processed. A temperature sensor senses the temperature within the thermokinetic mixing chamber. Once a set temperature is sensed, a first speed is changed to a second speed.

FIG. 1 shows a view of one embodiment of the disclosed thermokinetic mixer assembly. A temperature sensor 20 is connected to a thermokinetic mixing chamber MC. The temperature sensor 20 provides information to a programmable logic controller 20a which appears on a programmable logic controller display 20b. A drive motor 15 controls the speed of the shaft which rotates through the mixing chamber MC. The drive motor 15 is controlled by a variable frequency drive 20c. The variable frequency drive 20c also provides information to the programmable logic controller 20a which appears on the programmable logic controller display 20b. When a desired process parameter is met, the programmable logic controller 20a signals the variable frequency drive 20c to change the frequency of the electrical power supplied to the drive motor 15. The drive motor 15 changes the shaft speed of the shaft. The temperature sensor 20 can be a sensor to radiation emitted from batch components.

Figure 2:
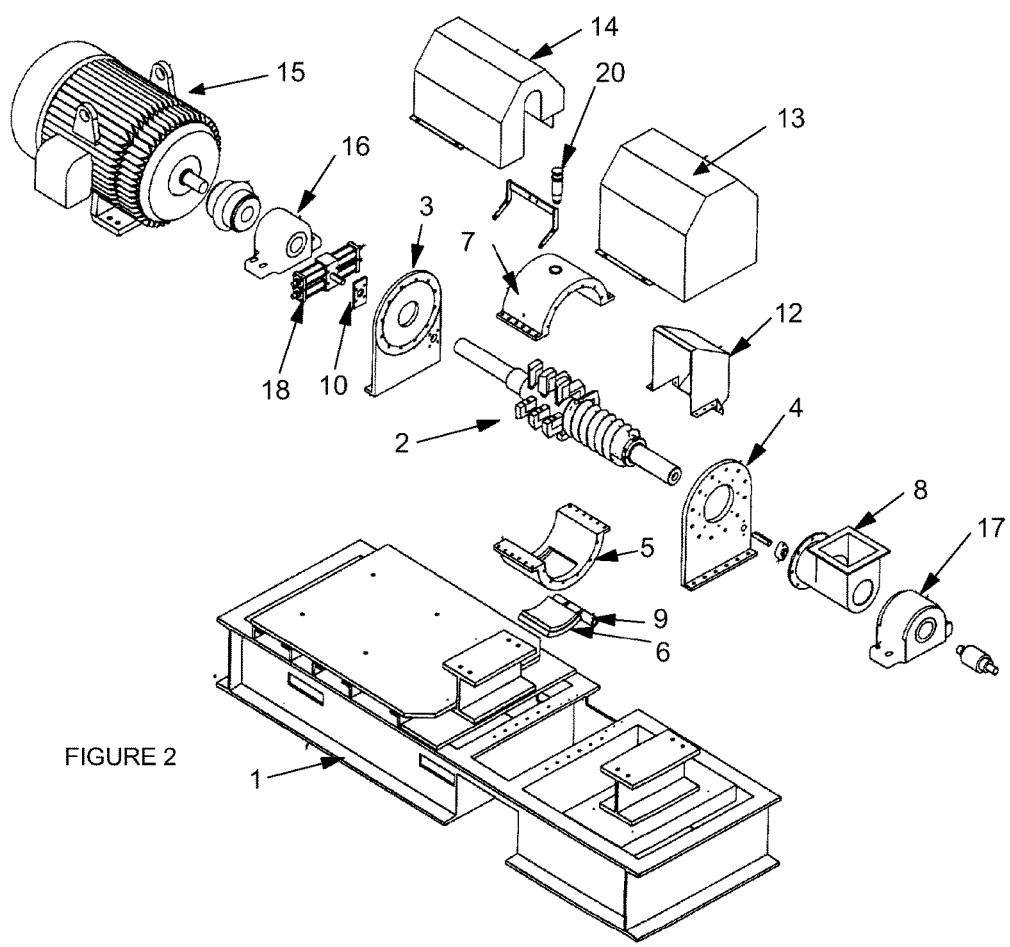
FIG. 2. An exploded view of the thermokinetic mixer.

FIG. 2 shows an exploded view of one embodiment of the thermokinetic mixer. A frame 1 supports associated components such that a shaft assembly 2 is inserted in an axis of a shaft hole through end plate 3 and a feed screw hole through end plate 4, the two end plates defining enclosing ends of a mixing chamber cylinder, the bottom portion of the cylinder defined by the inside surface of the lower housing 5. Lower housing 5 comprises a dropout opening closed off during operation with discharge door 6. The upper housing 7 comprises an upper part of the cylinder of the inside surface of the mixing chamber. The feed housing 8 is adapted to permit feeding of material to the feed screw of the shaft assembly so that such material is, in combination with the feed screw rotation, compressingly forced into mixing chamber from an external feed. Door 6 rotatably closes about discharge door pivot pin 9. End plate 3 has attached to it a rack & pinion cylinder 18 with spacer 10 interposed. At the top of housing 7 is mounted a bracket 11 with which to support an infrared temperature sensor 20 for the mixing chamber. Door guard 12 protects the sometimes high temperature door 6 from accidental human contact with dropout material. Rotary guard 13 and drive coupling guard 14 guard human operators from contact with rotating components during operation. Drive motor 15 is preferably an electric motor with sufficient power to accomplish the disclosed operation. The pillow blocks 16 and 17 support the shaft assembly 2.

In an example of a system in which the process parameters that determine shaft speed changes are measured in the mixing chamber and/or drive motor, FIG. 7 shows a block flow diagram of the disclosed process where a mixing chamber MC is connected by a shaft to a drive motor 42, where a variable frequency drive 41 controls the rotational speed of drive motor 42. In certain embodiments, shaft speed can be from 0 through 5000 RPM. Further, a programmable logic controller 40 determines and carries out a change in rotational shaft speed using a variable frequency drive 41 according to the disclosed process. The programmable logic controller 40 comprises setpoints entered by a user for determination of a need for changing a rotational shaft speed in drive motor 42 and to transmit to the variable frequency drive 41 a command to change such speed after rotational processing of the batch load has been added to the mixing chamber. The programmable logic controller may incorporate a microprocessor comprising memory incorporating a control program adapted to act upon achievement of setpoints entered by a user relying on sensor data transmitted from drive motor 42 and/or mixing chamber MC, and include a user interface such as a programmable logic controller display for a user to observe operating time and/or sensor data transmitted from drive motor 42 and/or mixing chamber MC. The programmable logic controller optionally comprises a method for a user to directly change motor shaft speeds upon consideration of predetermined process parameters (such as operation time) or upon comparison of predetermined process parameters with sensor data transmitted from drive motor 42 and/or mixing chamber MC (such as batch temperature, amperage draw, and shaft speed). The programmable logic controller optionally comprises an automated control method to change motor shaft speeds upon microprocessor operation at predetermined, stored process parameters (such as operation time) or upon comparison of predetermined, stored process parameters with sensor data transmitted from drive motor 42 and/or mixing chamber MC (such as batch temperature, amperage draw and shaft speed).

Figure 3:
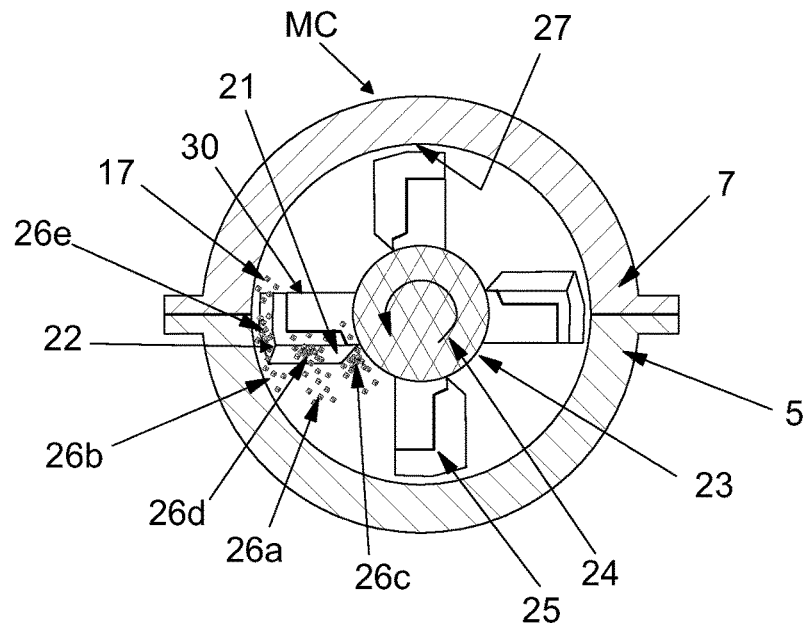
FIG. 3. A shaft-radial cutaway view of a thermokinetic mixing chamber.
Figure 4:
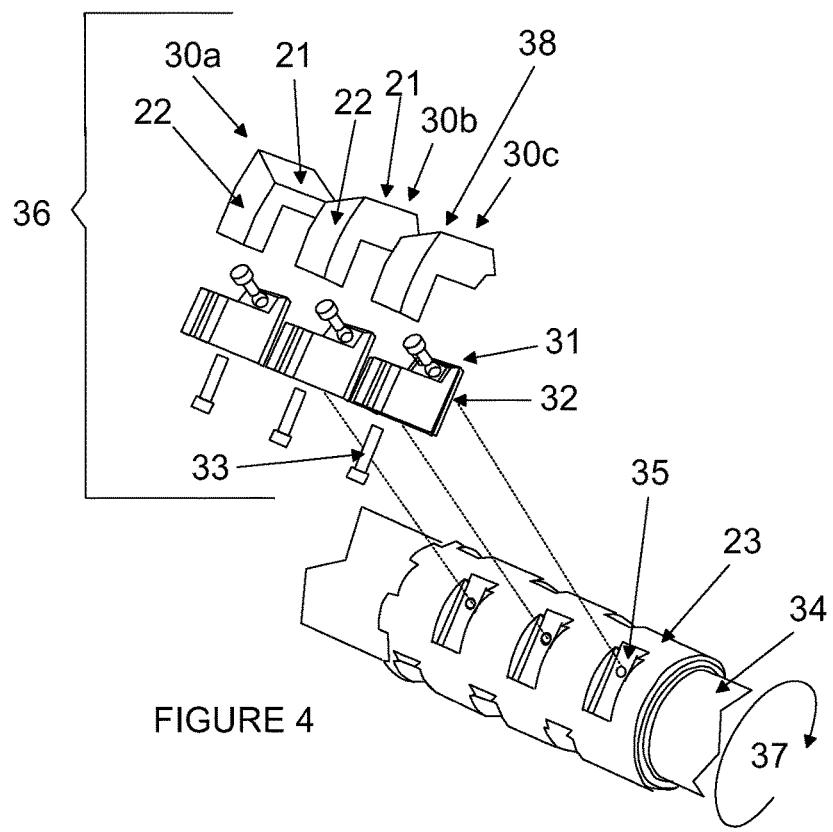
FIG. 4. An exploded view of the thermokinetic mixing chamber.

A description of components of one embodiment of a thermokinetic mixer for the disclosed process is shown in FIGS. 3 and 4. FIG. 3 shows a shaft-radial cutaway view of a mixing chamber MC for a thermokinetic mixer of the disclosure with halves 5 and 7 joined to form a cylindrical mixing cavity having shaft 23 rotating in rotation direction 24 in an axial length of the chamber. Shaft extensions 30 extend from their releasable connection on shaft 23 to a position near an inside surface 19. Shaft extension 30 comprises top face 22 and front face 21. Particles 26a-26e show impingement of such particles on shaft extension 30 and on inside surface 27, which impingement causes comminution and/or frictional heating of the particles by the shear generated by such impingement. Further, FIG. 4 is an exploded view of the extensions and mixing chamber shown in FIG. 3, where shaft extensions 30a, 30b, and 30c each having a top face 22 and a front face 21 defined upon a replaceable tooth which is adapted to be secured to foot section 31 by bolt 33. Section 31 is adapted to be replaceably fixed to shaft 23 (continued from motor shaft 37) at slot 35 by way of bottom section 32 of section 31. FIG. 4 shows that particles are generally moving in direction 38 when they encounter shaft extensions 30a to 30c. Shaft extension 30a is shown having its front face 21 aligned effectively opposing those of shaft extensions 30b and 30c.

With a typical batch process, a user will first select two components, which could include, for example, a thermolabile API and a polymer excipient. The user will then empirically determine the shear transition temperatures of the two components. The user will then set the process parameters (temperature, RPM, amperage draw, and time) in the programmable logic controller to change from the first speed to the second speed as is suitable for the shear transition temperatures of the components. Any of the setpoints entered by the user can be used as a stop point following the period of the second speed.

Figure 5:
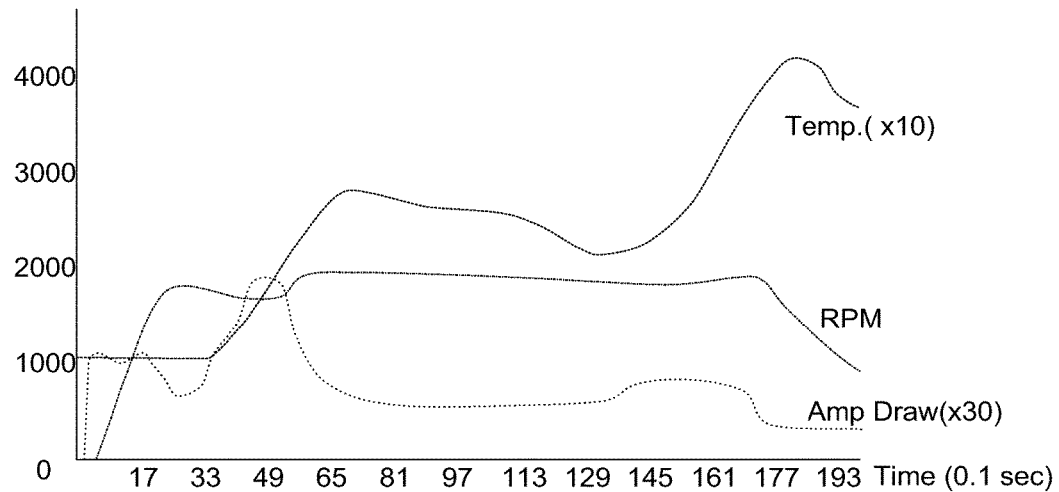
FIG. 5. Analysis of batch sensed temperature, shaft rotational speeding in RPMs, and amperage draw on the motor as a directly proportional measure of energy input into the batch at any moment with one rotational shaft speed.

FIG. 5 shows certain potential differences between the methods of the present disclosure, and that of a thermokinetic mixing method using a substantially single shaft speed. FIG. 5 shows a graph of batch sensed temperature, shaft rotational speed in RPMs, and amperage draw on the motor as a directly proportional measure of energy input into the batch at any moment in the processing. As a specific example the following composition was thermokinetically processed to form a batch of Griseofulvin:PVP (1:2 ratio) at a batch size of 60 grams. Griseofulvin represents a thermolabile API. PVP represents an excipient. A series of three tests is represented in FIG. 5 and was conducted in a thermokinetic mixer similar in construction to that shown in FIGS. 3 and 4, where front faces 21 project in a forward rotation direction with a side to side width of about 1.0 inches and are maintained at about 30 degrees away from a plane extending from an axis of the shaft 23 through a leading edge of the front faces 21 with a height of about 2.5 inches. The batch in FIG. 5 was processed under thermokinetic, autoheating conditions in which a substantially single shaft speed was used. The y-axis is applicable to temperature (values times 10) and shaft speed in RPM (value times 30). Time on the x-axis is in increments of 0.10 seconds. If the composition of this batch were thermokinetically mixed at rotational shaft speeds substantially higher than that shown in FIG. 5, i.e., at 2500 RPM and higher, inspection of the final product showed that it was unacceptably crystalline and insufficiently amorphous. This result would be unexpected to one of skill in the art. Higher shaft speeds are taught in the thermokinetic mixing art to assure better mixing, which did not occur at higher shaft speeds with these materials. When the example batch composition was processed as shown in FIG. 5, at lower rotational shaft speed, inspection of the final product showed that it was sufficiently amorphous and adequate for bioavailability. However, unacceptable thermal degradation of the thermolabile API occurred, which rendered the batch unacceptable.

In FIG. 5, at time zero, amperage draw immediately increased to 35 amps (1050 on the graph). Ejection of the batch was at about 17.6 seconds or where RPMs are shown to dramatically decline. The rotational shaft speed was set for 1800 RPMs and reached that speed within about 2 seconds from start. Within about 7 seconds, the batch temperature reached 260° F., the shear transition temperature for the excipient. Above the shear transition temperature, the excipient's resistance to shear dramatically decreased and energy delivered to the batch by impingement of particles and molten material on the extension surfaces and inside surface of the mixing chamber consequently also dramatically decreased (the amperage draw dropped to about one half when the shear transition temperature was reached in the batch temperature). From about 7 seconds to 16 seconds, the batch temperature of the composition was not rising while substantial energy continued to be absorbed by the batch. Such energy that did not result in increased temperature translated to thermal degradation of the thermolabile or heat sensitive components. This test confirms in general that once a significant amount of a component, i.e., greater than 5 weight percent, 10 weight percent, 20 weight percent, or 30 weight percent, in a thermokinetically melt blended batch reaches its shear transition temperature or melting point, a substantial amount of heat absorbed by the entire batch results in thermal degradation of thermolabile or heat sensitive components instead of increasing overall batch temperature. This is clearly shown in the time range from 7 through 16 seconds in FIG. 5, where batch temperature actually decreased with continuous energy input to the batch.

Figure 6:
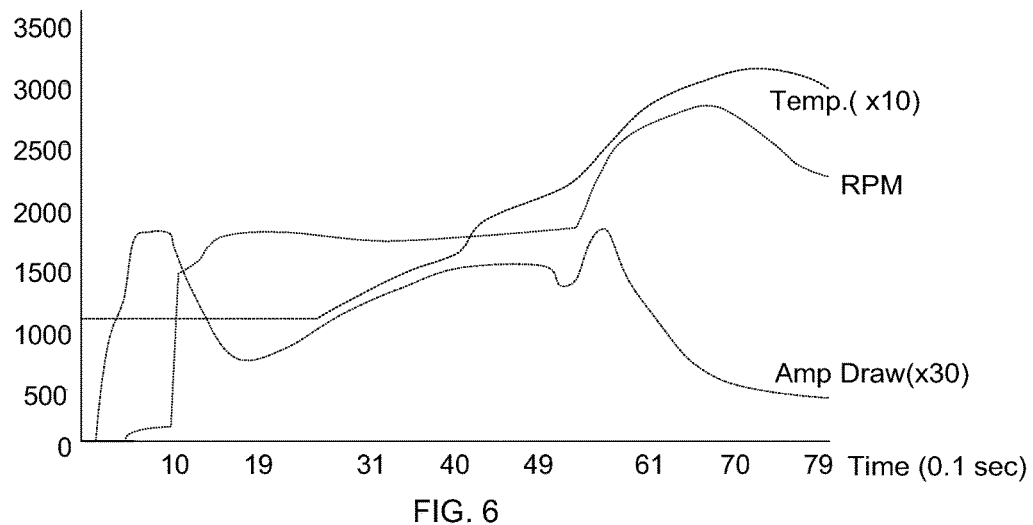
FIG. 6. Analysis of batch sensed temperature, shaft rotational speeding in RPMs, and amperage draw on the motor as a directly proportional measure of energy input into the batch at any moment with two rotational shaft speeds.

The same batch and thermokinetic mixer in FIG. 5 were used in FIG. 6, but two speeds were implemented through the continuous rotational batch processing. In FIG. 6, a programmable logic controller connected to an infrared sensor and a variable frequency drive was used for detecting a batch temperature, comparing the batch temperature to a predetermined setpoint, and automatically changing rotational shaft speed of the thermokinetic mixer to another speed for the duration of the process until the batch was released by way of opening a bottom dropout door. A first speed was set for 1800 RPM and a second speed was set for 2600 RPM. The predetermined setpoint for the batch temperature was chosen to be 200° F. as a substantial level below the excipient shear transition temperature. It is critical to effect a speed change before a substantial component's shear transition temperature is reached, and the system requires response time between the moment a sensed batch temperature is transmitted to the programmable logic controller and the shaft speed actually is changed. As shown in FIG. 6, no substantial energy input to the batch was diverted from overall batch temperature increase. The processed batch showed substantially complete amorphosity and no detectable thermal degradation of the API with an overall processing time of about 6.5 seconds. This time stands in dramatic contrast to that of the processing time of that in FIG. 5 at 17.6 seconds.

FIG. 6 indicates that shaft rotational speed for certain thermolabile components should be substantially increased at or before a substantial component or portion of a thermokinetically batch reaches a shear transition temperature or melting point, whereafter processing time should be minimized. In certain embodiments, a first speed should be increased by about 100 RPM, 200 RPM, 300 RPM, 400 RPM, 500 RPM, 600 RPM, 700 RPM, 800 RPM, 900 RPM, 1000 RPM, or more to a second speed. In other embodiments, a processing time after the second speed starts until the batch is released from the mixing chamber should be about 5 percent, 10 percent, 15 percent, 20 percent, 25 percent or more of the total time the batch was processed at the first speed.

It is well known in the art that impact of a particle on a surface imparts energy to the particle. It is a feature of thermokinetic, auto-heating mixers to provide impact on a particle containing polymers whereby imparted energy is translated partly into heat energy to soften and/or melt those polymers. However, the thermokinetic mixing art generally directs those skilled in the art to provide impact for particles in thermokinetic mixers in a manner that lacks fine control of translation of impact energy into heat energy. The present disclosure provides for and describes methods for such control. Highly cross-linked polymers and thermoset compounds are highly refractory to softening and melting for the same reason they are preferred, i.e., they resist breaking down. Yet, they are shown to be of value in some combinations of components processed with thermokinetic mixing. Indeed, thermokinetic mixing is essentially the only way to process highly cross-linked polymers and thermosets due to their resistance to melting and blending in any other manner. In the thermokinetic mixing art, increasing rotational shaft speed and/or processing time were understood to be the method by which melt-resistant polymers could be induced to translate sufficient impact energy to heat energy to effect a softened or molten state for further processing. The present embodiment discloses an apparatus and methods by which impact energy translation to heat energy can be effectively controlled.

Two primary impact surfaces, the front face and the top face of a shaft, control impact translation to heat energy in a thermokinetic mixer. Those two surfaces are the facial portions of the shaft extensions that intrude into the outer 30 percent or less of volume of the mixing chamber (the volume is referred to hereafter as the "main processing volume"; it includes a most restricted zone of about one inch inward radius from the inside cylindrical wall of the mixing chamber) and the inside cylindrical surface of the mixing chamber itself. Changing the inside cylindrical surface of the mixing chamber is not a practical option—that surface, being stationary, must remain smooth and cylindrically uniform to resist buildup of molten materials and to allow for skidding and sliding autoheating contact with particles being moved through the mixing chamber.

The present disclosure uses variations in the top face of the shaft extensions that intrude into the main processing volume to control translation of rotational shaft energy delivered to the extensions into heating energy within particles impacting the portions. It has been found that varying the width and angle away from a shaft axis plane for the main facial portion provides a controllable variation in shear delivered to a particle impacting the portion, which in turn provides control over shaft energy translated into heat energy available for softening or melting a polymer part of a particle in a thermokinetic mixing chamber.

Referring again to FIGS. 3 and 4, it has been found that providing particles within the mixing chamber a cumulative experienced shear which is determined by the shape and dimensions of a rotation-directed facial surface of extensions from the shaft and the inside surfaces of the mixing chamber results in the autoheating phenomena of thermokinetic mixing. Substantially all the particles within a mixing chamber during shaft rotation inhabit the outer 30 percent of the volume of the internal space, i.e., the centrifugal force of the rotation of the extensions maintains the particulates and molten materials away from a central volume of the mixing chamber. Thus, the effective thermokinetic mixer must be designed so that distal end parts of the shaft extensions are formed to accomplish the three functions of direct high shear (on the end part front face of the extension), indirect high shear (on the inside surfaces of the mixing chamber), and centrifugal maintenance of material in the outer volume of the mixing chamber. The top faces of shaft extensions 30a to 30c form a substantially vertical rectangle arranged at an angle away from a plane passing through an axis of shaft 23. It has been found that changing the width, angle, or varying the shape of the simple rectangle or arcuate paddle of the shaft provides an unexpected improvement and control over cumulative shear delivered to particles within a mixing chamber of a thermokinetic mixer, which, in turn, provides control over imparted heat energy and desired heat input to heat sensitive or thermolabile components in a processed batch.

For these specific comparisons of the operation of thermokinetic mixers with several configurations of a main facial portion, it is assumed that energy input through the shaft and the shaft rotational speed is about the same and that the number of shaft extensions and their spacing along the length of the shaft within the mixing chamber is substantially the same. Thus, the comparisons will show the effect of changing the shapes of the main facial portion.

In general, decreasing the width relative to the length of the main facial portion increases shaft energy translated into heat energy available for softening or melting a polymer part of a particle in a thermokinetic mixing chamber. The width must be above a minimum contact width so that a particle experiences a sliding impact along the width, the particle is induced into a "skid" or energy imparting frictional contact, rolling and sliding at the period of time for impact on the portion. Mere normal glancing impact of a particle on a surface is relatively ineffective in imparting thermokinetic, autoheating energy for softening or melting. Yet, easily melted and heat-labile or heat sensitive polymers in some cases are sometimes processed with a main facial portion providing just such glancing impact to provide more control over heat application to such components. Consistent with this teaching, polymers refractory or resistant to softening or melting by application of heat are often processed with a main facial portion of minimum width (at least 0.25 inches) aligned at a minimum angle back from a shaft axial plane (for example, at least 10 degrees or at least 15 degrees) providing a contact time for essentially the same energy input, whereby distribution of that energy into skidding and rotational motion improves autoheating of the particle's polymer content.

A design of a shaft extension currently found in the Draiswerke Gelimat® thermokinetic mixer has the cross section 50 shown in FIG. 8, having a rounded main facial portion 51 and an overall substantially spiral shape with a width of about 2 inches. Relative shear 52 shown in a number of shortened arrows directed at the main facial portion 51 is not substantial for this design. Thus, this device has been relatively costly in terms of increased processing time and shaft power to generate sufficient thermokinetic heating to melt-blend polymers with substantial resistance to softening or melting. As such, it is relatively inadequate for processing heat labile or heat sensitive polymers having such resistance. There has been no suggestion in the thermokinetic mixing art that changing the width or angle of the main facial portion relative to a shaft axial plane would have any affect on thermokinetic processing of polymers. The present disclosure discloses such embodiments in FIGS. 9 through 12.

FIGS. 9 through 12 respectively show main facial portion cross sections 53 through 56 having main facial portions 57 through 60 with identical widths at angles of about 15 degrees, 30 degrees, 45 degrees and 60 degrees back from a shaft axial plane for the extensions which they represent. The projected widths on that shaft axial plane of main facial portions 57 through 60 are shown respectively in lengths 65 through 68 and are directly related to relative shears 61 through 64, where an increasing angle of a main facial portion relative to a shaft axial plane with identical width decreases the projected width onto the plane and unexpectedly increases relative shear for the same shaft power input, rotational shaft speed and extension spacing and arrangement on the shaft. With this disclosure, it is now possible to control autoheating by delivered shear in the extensions of a thermokinetic mixer. Decreasing the widths of main facial portions while maintaining the angle relative to a shaft axial plane maintains total heat input into a thermokinetically processed batch in the mixers but increases shear upon any individual particle by reducing projected length along the shaft axial plane.

Thus, the shear strength of polymers processed by way of thermokinetic, autoheating mixing and blending can now be matched to the relative shear energy imparted by the shaft extensions in the mixing chamber. A further design refinement is desirable where, as is quite common, polymer components in a batch comprise both high shear and low shear polymers. Providing a main facial portion suited for a high shear component imparts shear energy which may deliver too much heat energy to low shear components. In such a case, the low shear component tends to soften and roll along the width of the main facial portion, further increasing the heat generated, while the high shear components tend to leave that surface more readily. Such a circumstance could tend to cause incomplete mixing with the high shear components insufficiently melted or overheating of low shear components. There is yet a further need for designs of a main facial portion that achieve an optimal shear delivery to high and low shear components in a thermokinetic batch.

It has been found that increasing the width of the main facial portion achieves this optimization. At an angle of between 15 to 80 degrees from a shaft axis plane, and the main facial portion having a width of at least 0.75 inches, provides sufficient path travel for both high and low shear polymer components in a batch so that the high shear components remain in sliding and skidding contact with the main facial portion long enough to generate heat and absorb heat from lower shear components to become softened and thereby blend with the low shear components.

Alternate designs for the main facial portion are shown in FIGS. 13 through 17, respectively, showing main facial portion cross sections 69, 72, 76, 80, 84, and 87. FIG. 13 shows cross section 69 comprising a leading acute surface 70 extending rearward to obtuse surface 71, providing a first low shear surface followed by a higher shear surface. FIG. 14 shows cross section 72 comprising a leading acute surface 73 extending rearward to 90 degree surface 74, which in turn extends rearward to tailing acute surface 75, providing a first low shear surface followed by a higher shear surface and a lower shear surface. FIG. 15 shows cross section 76 comprising a leading acute surface 77 extending rearward to obtuse surface 78, which in turn extends rearward to tailing acute surface 79, providing a first low shear surface followed by a higher shear surface and a lower shear surface. FIG. 16 shows cross section 80 comprising a leading obtuse surface 73 extending rearward to acute surface 74, which in turn extends rearward to tailing obtuse surface 75, providing a first high shear surface followed by a lower shear surface and a high shear surface. FIG. 17 shows cross section 84 comprising a leading and rising arcuate surface 85 extending rearward to a tailing and reducing arcuate surface 86 degree surface 74, which in turn extends rearward to tailing acute surface 75, providing a first low shear surface followed by a higher shear surface and a lower shear surface. FIG. 18 shows cross section 87 comprising a leading acute surface 88 and a tailing acute surface 89, providing a first low shear surface followed by a higher or lower shear surface, depending on the shear of the batch components.

In light of the above teaching of these embodiments, the top face 22 of FIG. 4 is a significant element in providing thermokinetic contact with particles in the mixing chamber and causing them to impact the inside cylindrical surface of the mixer.

Figure 19:
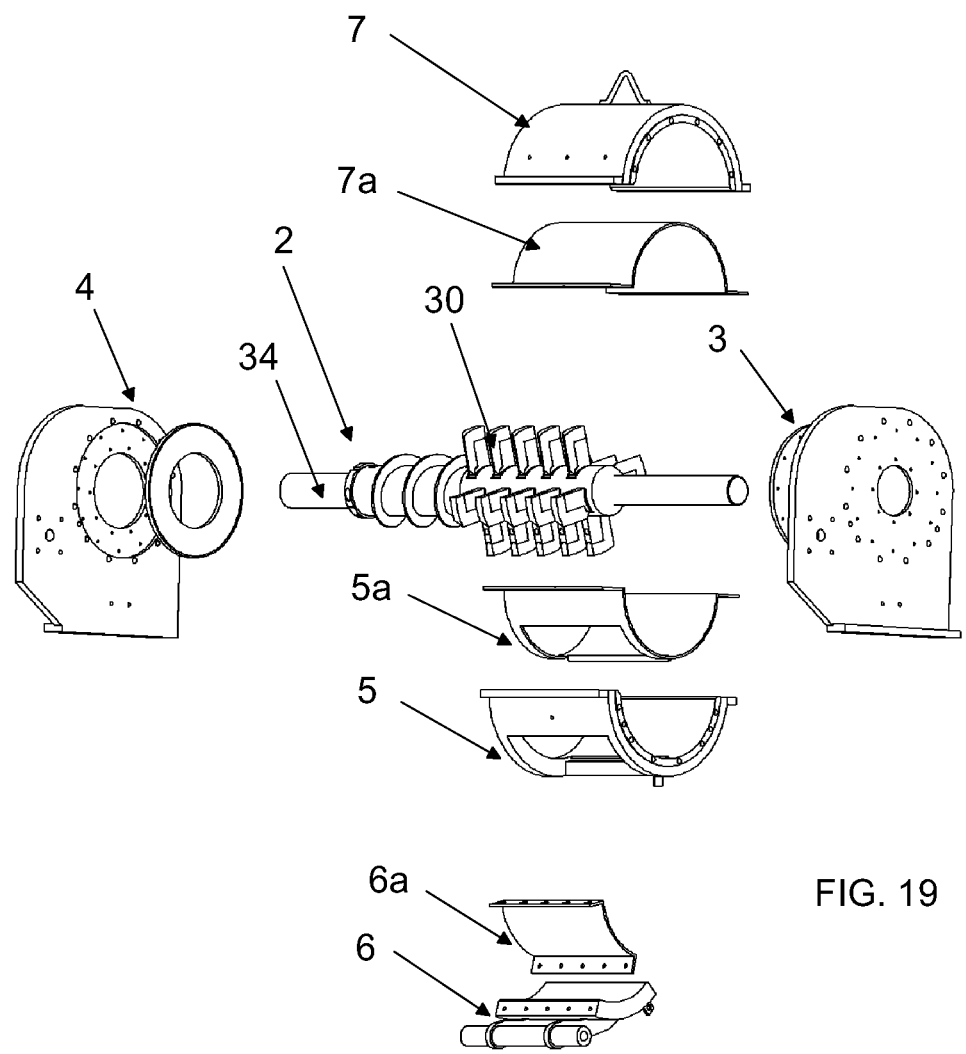
FIG. 19. An exploded view of the thermokinetic mixer showing internal liner pieces.

FIG. 19 shows another significant embodiment of the thermokinetic mixer of the present disclosure, in that halves 5 and 7 and door 6 are respectively interiorly lined by interior liner pieces 5a, 7a and 6a. The liner pieces are adapted to intimately lie adjacent to inside surfaces of halves 5 and 7 and door 6 during operation of the mixer, thereby providing any of a diverse set of thermokinetic frictional contact surfaces desired for accelerated particles, such desired surfaces selected from among any appropriate or optimized materials for liner pieces 5a, 7a and 6a. FIG. 19 shows in exploded view the liner pieces 5a, 7a and 6a separated from their adjacent (as installed) parts. Bolting the halves 5 and 7 together cause liner pieces 5a and 7a to secure to line the inside surfaces of those halves 5 and 7. Holes in end sections of liner piece 6a allows for bolted connection of it to door 6. In thermokinetic mixers known to those of skill in the art, the inside surfaces of the mixing chamber were limited to those steel alloys with sufficient mechanical and thermal strength required for encasing and enclosing the thermokinetic operation of such mixers. Therefore, known thermokinetic mixers were limited in their processing capabilities to only those mixtures which would not excessively adhere to a smooth inside surface of steel alloy of the mixing chamber and which, at the same time, would impinge beneficially on those surfaces to provide frictional heating of particles in the mixture. Further, even relatively slight wear on the inside surfaces of the mixing chambers of thermokinetic mixers can dramatically alter the efficacy of the generation of thermokinetic heating of chambered particles, in that the distance between the shaft extensions and the inside surface of the mixing chamber is specifically designed to optimize thermokinetic heating by the interaction of particles moving between the inside surface of the mixing chamber and the shaft extensions. Thus, such slight wear can require that the entire, relatively expensive set of halves 5 and 7 to be replaced in such thermokinetic mixers. The present embodiment eliminates such excessive cost. Liner pieces 5a, 7a and 6a are relatively much less in cost to replace than halves 5 and 7 and door 6. Replacement of the liner pieces is quite simple and fast. Preferred liner piece composition includes stainless steel (alloys with greater than 12 weight percent chrome) and other such steel alloys, titanium alloys (such as nitrided or nitride-containing titanium), and wear and heat resistant polymers (such as Teflon®). It is another embodiment of the present disclosure to provide non-smooth inside surfaces for liner pieces 5a, 7a and 6a, such as parallel or spiral grooving about the inside cylindrical surfaces of liner pieces 5a, 7a and 6a, surface texturing, and/or electropolishing. Such materials and texturing for liner pieces 5a, 7a and 6a are intended to obtain an optimum or desirable balance of characteristics which will reduce undesirable adhesion of thermokinetically melted particles and/or promote thermokinetic frictional contact of mixing chamber particles in their travel among the shaft extensions and the inside surfaces of the liner pieces 5a, 7a and 6a.

In a further embodiment of the present disclosure whereby materials or texturing of liner pieces 5a, 7a and 6a are selected to obtain the objects of thermokinetic mixing, shaft extension portions comprising the front and top impact faces of the shaft extensions are adapted by way of material composition and/or texturing similar to those changes just disclosed for the inside surfaces of liner pieces 5a, 7a and 6a.

Another feature of the present disclosure is that the top face of the shaft extensions, i.e., those which extend at least with a slight elevation rearward above the height of the front face of the shaft extension to form a ramp structure upon which chambered particles impinge (faces 22 of FIGS. 3 and 4), are the primary location of wear among the inside surfaces of the mixing chamber. The consequences of this discovery are considerable with respect to the design of shaft extensions in thermokinetic mixers. It has been found that such a top face has a function very different than that of the front face. A front face of a shaft extension drags a particle along its rearward directed width, causing the particle to be driven substantially in a direction of an axis of the drive shaft. Such an axis-driven particle will then tend to engage yet another front face of a shaft extension of a rearward and next line of shaft extensions. The motion of particles in contact with a top face of a shaft extension driven by shaft rotation is very different, imparting in such motion a substantially greater frictional, thermokinetic energy to a particle than the front face of the shaft extension.

Figure 20:
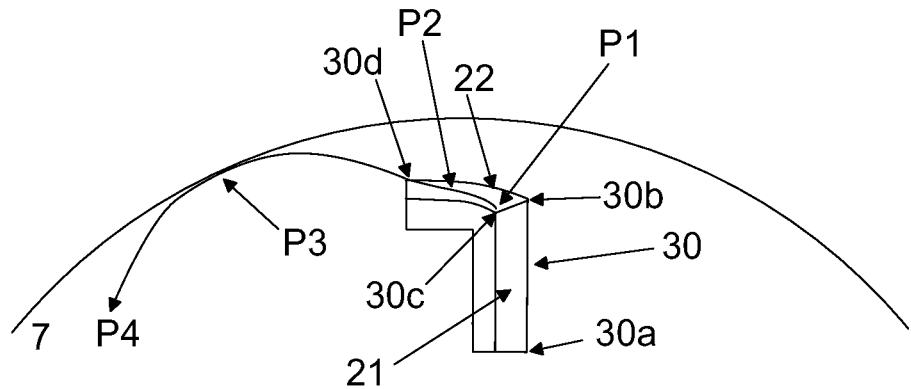
FIG. 20. A generalized side view of a shaft extension's top face interaction with an inside surface of a mixing chamber.

FIG. 20 shows a side view (a view in the direction of the axis of a shaft to which it is mounted) of a removable portion of a shaft extension 30 showing a front face 21 and top face 22. Reference elevations 30b to 30d are measured from a base level 30a. Neither front face 21 or top face 22 are shown in plan view but rather are shown with their projections upon the side shaft-axial view. Top face 22 comprises a front edge rising from elevation 30c to 30b and thereafter sweeping rearward and upward to similarly inclined rear edge with a highest elevation 30d. Only a part of the inside surface of half 7 is shown as separated from top face 22 and portions P1 to P4 represent the path of a particle impinging first upon top face 22 and then upon the inside surface of half 7. It has been found that the area of greatest wear on any inside surface of the mixing chamber is along the rearward area from the front edge represented by the line from elevations 30c to 30b, i.e., the impact point of a particle at portion P1. A major portion of kinetic energy is clearly translated to frictional heating to the particle in that area as evidenced by the substantial wear on such hardened surfaces. Top face 22 rises more rapidly at its far edge along elevations 30b to 30d than along the near edge starting at elevation 30c, resulting in a relatively long frictional travel path of the particle along portion P2 and being ramp-launched from elevation 30d toward the inside surface of half 7. Upon frictional, spinning, and dragging contact with the inside surface of half 7 at portion P3, the extensively heated particle rebounds from the inside surface of half 7 to again contact a top face of another shaft extension. The length of portion P2 substantially controls required frictional heating time for thermokinetic mixing and melting for a batch of particles within the mixing chamber of the present disclosure. The present disclosure comprises selecting a shaft extension which provides to an impinging particle in thermokinetic mixing a top face contact path of longer or shorter length and angle of deflection to thereby control a substantial or majority of frictional heating contact of chambered particles to a desired batch temperature.

Figure 21:
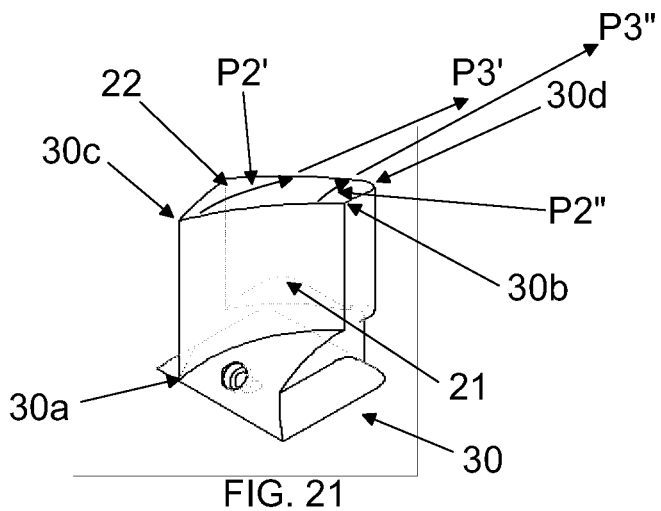
FIG. 21. A perspective view of a shaft extension with variable top face path lengths.

FIG. 21 shows a perspective view of a specific embodiment of the shaft extension of FIG. 20 having a concave front face 21 and a top face 22 capable of producing variable lengths of portions P2' (longer) and P2" (shorter) respectively for portions P3' and P3". In certain embodiments, the top face 22 comprise a convex surface with a radius of about 4.5 inches extending from its front, leading edge to its rearmost edge.

In certain embodiments, a shaft extension providing a relatively long frictional contact path for particles being processed by the mixer of the present disclosure are preferred for providing shortened processing times, i.e., to heat a batch to a desired temperature as quickly as possible. Such control of heating and processing times is directly applicable to the disclosed process of two step continuous thermokinetic mixing, whereby increasing rotational shaft speed will more swiftly impart frictional heating for melting energy to the particles more refractory or resistant to lower speed heating. It has been found that non-uniformity of materials in a batch processed thermokinetically, i.e., either by composition or particle size, results in greater or lesser frictional path contact with the insides of the mixing chamber. Particles more resistant to melting, either by way of higher melting temperatures or hardness, will rebound more quickly from frictional contact with the inside surfaces of a thermokinetic mixer and thereby require more processing time than less refractory particles. Thermokinetic mixing to a final, desired processing consistency for heat labile or heat damageable components generally favors reaching a target batch temperature as quickly as possible. Certain embodiments of the present disclosure provide short, medium, long or mixed lengths of particle frictional contact paths along a top face of a shaft extension, either by way of a single or multiple processing shaft speeds, to achieve the more effective mixing of certain thermolabile components.

Figure 22:
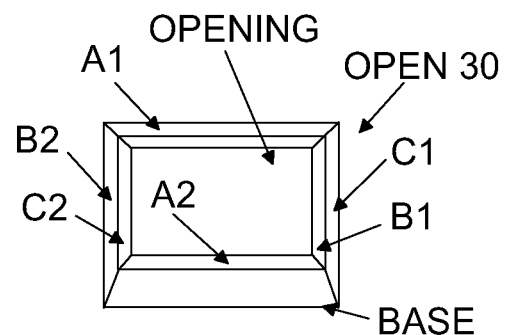
FIG. 22. An alternative design of a front face of a shaft extension.

It is well known to those in the art that the topmost surfaces of shaft extensions in the Draiswerke mixers are merely arcuately tapered and smoothed ends of a generally sinous shaft extension. As such, the ability of such mixers to provide substantial top face shearing, frictional heating to thermokinetic mixing chamber particles is essentially minimized. To accomplish additional top face-like frictional paths for particles in the mixing chamber and to accomplish other objects of the present disclosure, FIG. 22 discloses a frontal view of an OPEN 30 shaft extension having a central OPENING so that particles can pass through it during processing and impinging on identically rearwardly angled pairs of surfaces A1/A2, B1/B2 and C1/C2. It will be appreciated that surfaces A1/A2 together act upon particles as a top face and that surfaces B1/B2 and C1/C2 act upon particles as front faces. FIG. 22 more generally discloses that shaft extensions may be formed in a donut or toroid shape or in the shape of a diamond with a central opening to accomplish the more effective mixing of certain thermolabile components.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

I claim:

1. A method of melt-blending a composition of two or more ingredients comprising one or more crystalline, thermolabile active pharmaceutical ingredients (API's) and one or more pharmaceutically acceptable excipients or carriers, wherein a thermokinetic compounding of the ingredients takes place when the ingredients are heated by way of being processed at high rotational speeds of shaft extensions on a motor driven shaft in a mixing chamber of a thermokinetic mixer, whereby the resulting composition forms a melt blended pharmaceutical composition with a substantially higher amorphosity and reduced crystallinity of the API's than in the original ingredients, the method additionally comprising operating the motor driven shaft for a first time period at a first lower speed until achieving a predetermined parameter, at which time the shaft speed is adjusted to a second higher speed for a second time period, wherein the mixing process is uninterrupted between the first and second time periods.

2. The method of claim 1, wherein the second time period is five percent or more of the first time period.

3. The method of claim 1, wherein the second time period is 10 percent or more of the first time period.

4. The method of claim 1 wherein the predetermined parameter is achieved, at the end of the first time period, substantially before a mixing chamber temperature reaches a shear transition temperature or a melting point of any substantial component of the ingredients.

5. The method of claim 1, wherein the end of the first time period is a predetermined time period and a change to the second speed is made automatically by the thermokinetic mixer at the end of the first time period.

6. The method of claim 1, wherein the end of the first time period is substantially before a mixing chamber temperature reaches the shear transition temperature of an API in the ingredients.

7. The method of claim 1, wherein the end of the second time period is substantially before an API experiences substantial thermal degradation.

8. The method of claim 1, wherein the first lower speed is greater than 1000 revolutions per minute and the second higher speed is 200 to 400 revolutions per minute greater than the first lower speed.

9. The method of claim 1, wherein the first lower speed is greater than 1000 revolutions per minute and the second higher speed is 200 to 1000 revolutions per minute greater than the first lower speed.

10. The method of claim 1, wherein the first lower speed is greater than 1000 revolutions per minute and the second higher speed is 200 to 2500 revolutions per minute greater than the first lower speed.

11. A method of compounding an active pharmaceutical ingredient and at least one polymeric pharmaceutically acceptable excipient to produce a heterogeneously homogenous composition, the method comprising thermokinetic mixing of the active pharmaceutical ingredient and at least one polymeric pharmaceutically acceptable excipient in a sealed mixing chamber of a thermokinetic mixer at a first lower speed effective to increase a batch temperature of the mixture, and, at a time point at which the batch temperature is near a shear transition temperature of any active pharmaceutical ingredient or polymeric pharmaceutically acceptable excipient in the mixture, as detected by an increase in power usage of the thermokinetic mixer, and then increasing the mixer angular rotation to a second higher speed for a second time period, whereafter the thermokinetic mixer is stopped to produce a heterogeneously homogenous composition, wherein the mixing is accomplished without stopping the mixing or opening the sealed mixing chamber, whereby a desired amorphosity of an active pharmaceutical ingredient of a resulting composition is achieved at less total mixing time than when using a single thermokinetic mixing speed.

* * * * *